(12) United States Patent
Hight, III (10) Patent No.: US 6,994,823 B2
(45) Date of Patent: Feb. 7, 2006

(54) APPARATUS AND METHOD FOR VENTILATING ENDOSCOPE SOAKING BASINS

(75) Inventor: H. Thomas Hight, III, Kennesaw, GA (US)

(73) Assignee: Next Step Technologies, LLC, Kennesaw, GA (US)

( * ) Notice: Subject to any disclaimer, the term of this patent is extended or adjusted under 35 U.S.C. 154(b) by 512 days.

(21) Appl. No.: 10/056,701

(22) Filed: Jan. 25, 2002

(65) Prior Publication Data

US 2002/0068028 A1    Jun. 6, 2002

Related U.S. Application Data

(63) Continuation-in-part of application No. 09/702,465, filed on Oct. 31, 2000, now Pat. No. 6,361,751.

(60) Provisional application No. 60/296,853, filed on Jun. 9, 2001.

(51) Int. Cl.
*A61L 9/00*  (2006.01)
*A61L 2/00*  (2006.01)
*B01D 11/02* (2006.01)
*B08B 9/00*  (2006.01)
*B65D 83/10* (2006.01)

(52) U.S. Cl. .............................. 422/28; 422/1; 422/30; 422/32; 422/33; 422/261; 422/292; 422/300; 134/22.1; 134/22.11; 134/22.12; 134/22.14; 134/22.18; 134/22.19; 134/34; 206/364; 206/438

(58) Field of Classification Search .................. 422/1, 422/28, 30, 32–33, 261, 292, 300–302, 905; 134/22.1, 22.11, 22.12, 22.14, 22.18, 22.19, 134/34, 42; 206/364, 438; 454/49–67
See application file for complete search history.

(56) References Cited

U.S. PATENT DOCUMENTS

| | | | | |
|---|---|---|---|---|
| 3,983,996 A | * | 10/1976 | Hendren, III | 206/363 |
| 4,053,280 A | * | 10/1977 | Salisbury | 206/363 |
| 4,288,882 A | * | 9/1981 | Takeuchi | 15/88 |
| 5,494,637 A | * | 2/1996 | Barlow | 422/28 |
| 5,534,221 A | * | 7/1996 | Hillebrenner et al. | 422/33 |
| 5,882,589 A | * | 3/1999 | Mariotti | 422/28 |
| 5,882,590 A | * | 3/1999 | Stewart et al. | 422/28 |
| 6,203,756 B1 | * | 3/2001 | Lin et al. | 422/33 |

FOREIGN PATENT DOCUMENTS

GB          2 244 919 A   * 12/1991

OTHER PUBLICATIONS

Internet print-out for the definition of the term "section".*

* cited by examiner

*Primary Examiner*—John Kim
*Assistant Examiner*—Monzer R. Chorbaji
(74) *Attorney, Agent, or Firm*—Smith, Gambrell & Russell (57) ABSTRACT

The present invention provides an apparatus for removing fumes from an endoscope disinfecting apparatus configured for disinfecting an endoscope with a disinfecting solution. In architecture, the exhaust system includes a fan housing, a fan disposed within the fan housing, an exhaust hose connected to the fan housing, and wherein the exhaust system is connected to the endoscope disinfecting apparatus.

18 Claims, 8 Drawing Sheets

APPARATUS AND METHOD FOR VENTILATING ENDOSCOPE SOAKING BASINS

CROSS REFERENCE TO RELATED APPLICATIONS

This application is a continuation-in-part of U.S. Utility Application entitled, "Apparatus and Method for Disinfecting an Endoscope," having Ser. No. 09/702,465, filed Oct. 31, 2000, now U.S. Pat. No. 6,361,751 which is entirely incorporated herein by reference.

This application claims priority to copending U.S. Provisional Application entitled, "Apparatus and Method for Ventilating Endoscope Soaking Basins," having Ser. No. 60/296,853, filed Jun. 9, 2001, which is entirely incorporated herein by reference.

TECHNICAL FIELD

The present invention is generally related to endoscopes, and more particularly, is related to an apparatus and method for ventilating endoscope soaking basins.

BACKGROUND OF THE INVENTION

Recent improvements in endoscope technology have provided great advances in the practice of medicine. These advances in endoscope technology have enabled medical practitioners to increase the ability to research patient conditions and aid in the diagnosis of heretofore difficult to diagnose conditions. Once the difficult to diagnose conditions are identified, the correct medical treatment can be applied with confidence. In addition to diagnostic applications, endoscopes are used to treat a growing number of conditions.

Endoscopes are widely used on a large variety of organs in the human body, as well as in veterinary applications. These organs include, but are not limited to, digestive, respiratory, urinary, gynecological, orthopedic and otorhinolaryngological systems. The endoscopes used on these various organs of the human body are so expensive that they cannot simply be discarded after a single use on a single patient, but instead must be applied successfully to many patients. Therefore, the used endoscope must be thoroughly cleaned and disinfected before being available for use on another patient.

Currently, there are two types of endoscope cleaning and disinfecting apparatuses and methods. The first is generally utilized in well-financed operations, such as big hospitals. These well-financed institutions generally use an automatic endoscope cleaning and disinfecting machine costing several thousand dollars. The automatic cleaning and disinfecting machine operates much like a dishwasher in cleaning and disinfecting the endoscope. These machines can be costly to operate and repair.

The second type of endoscope cleaning apparatus is a soaking basin. The soaking basin type endoscope cleaning apparatus utilizes a basin to soak an endoscope in a cleaning solution, followed by soaking the endoscope in a disinfecting solution. The soaking basins are usually box shaped containers, with lids. The disinfecting solution is typically glutaraldehyde, a toxic substance. There are numerous problems with using glutaraldehyde. The used and discarded solution is toxic to the environment. The larger the quantity of glutaraldehyde used in the disinfecting process, the more the environmental damage from the discarded solution. Decreasing the quantity of glutaraldehyde needed for this process would benefit the environment.

While being used for soaking the instruments, glutaraldehyde evaporates, creating noxious and toxic fumes that build up within the soaking basins. Endoscope cleaning staff must wear badges monitoring their exposure to glutaraldehyde fumes. In order to try to limit human exposure to these toxic fumes, the soaking basins are often located in ventilation hoods having air removal fans for removing those fumes that escape from the soaking basins when their lids are removed. Despite provision of the hoods and fans, many endoscope cleaning and disinfecting rooms still smell strongly of glutaraldehyde.

Because ventilation hoods are not one-hundred percent efficient in removing those fumes that escape from the soaking basins when the lids are removed, it is desirable to maintain the amount of vapors present in the soaking basins at the lowest level possible at all times. Thus, a heretofore unaddressed need exists in the industry to address the aforementioned deficiencies and inadequacies.

SUMMARY OF THE INVENTION

The present invention provides an apparatus for removing fumes from an endoscope disinfecting apparatus configured for disinfecting an endoscope with a disinfecting solution. The said exhaust system includes a fan housing, a fan disposed within the fan housing, an exhaust hose connected to the fan housing, and wherein the exhaust system is connected to the endoscope disinfecting apparatus.

Other features and advantages of the present invention will become apparent to one with skill in the art upon examination of the following drawings and detailed description. It is intended that all such additional features and advantages be included herein within the scope of the present invention.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Reference will now be made in detail to the description of the invention as illustrated in the drawings. Although the invention will be described in connection with these drawings, there is no intent to limit it to the embodiment or embodiments disclosed therein. On the contrary, the intent is to include all alternatives modifications, and equivalents included within the scope of the invention as defined by the appended claims.

Figure 1:
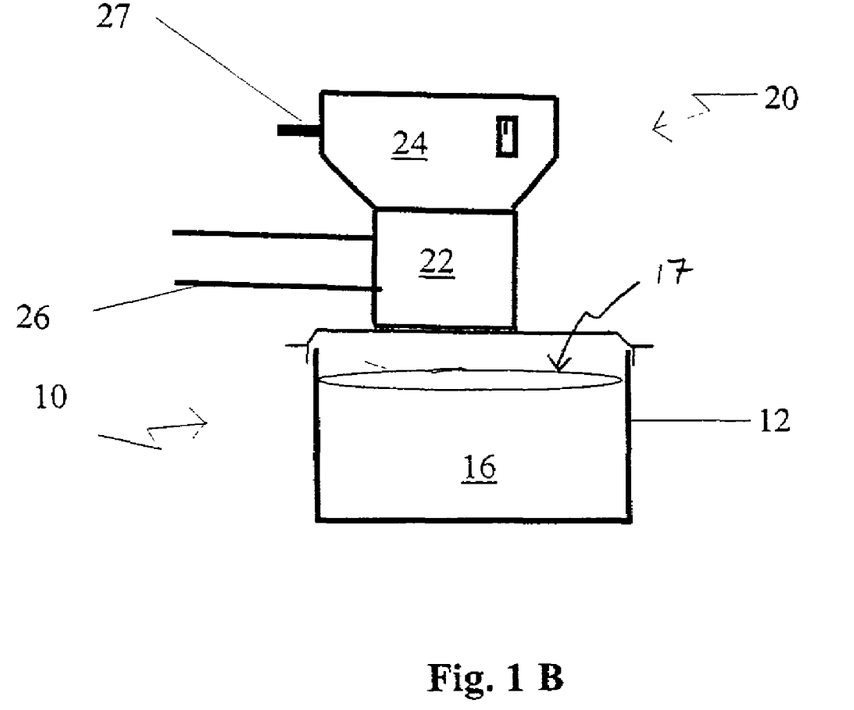
FIG. 1A is a side view of an endoscope disinfecting apparatus that includes an embodiment of the ventilation system of the present invention.
FIG. 1B is a side view of an endoscope disinfecting apparatus that includes an embodiment of the ventilation system of the present invention.
Figure 1A:
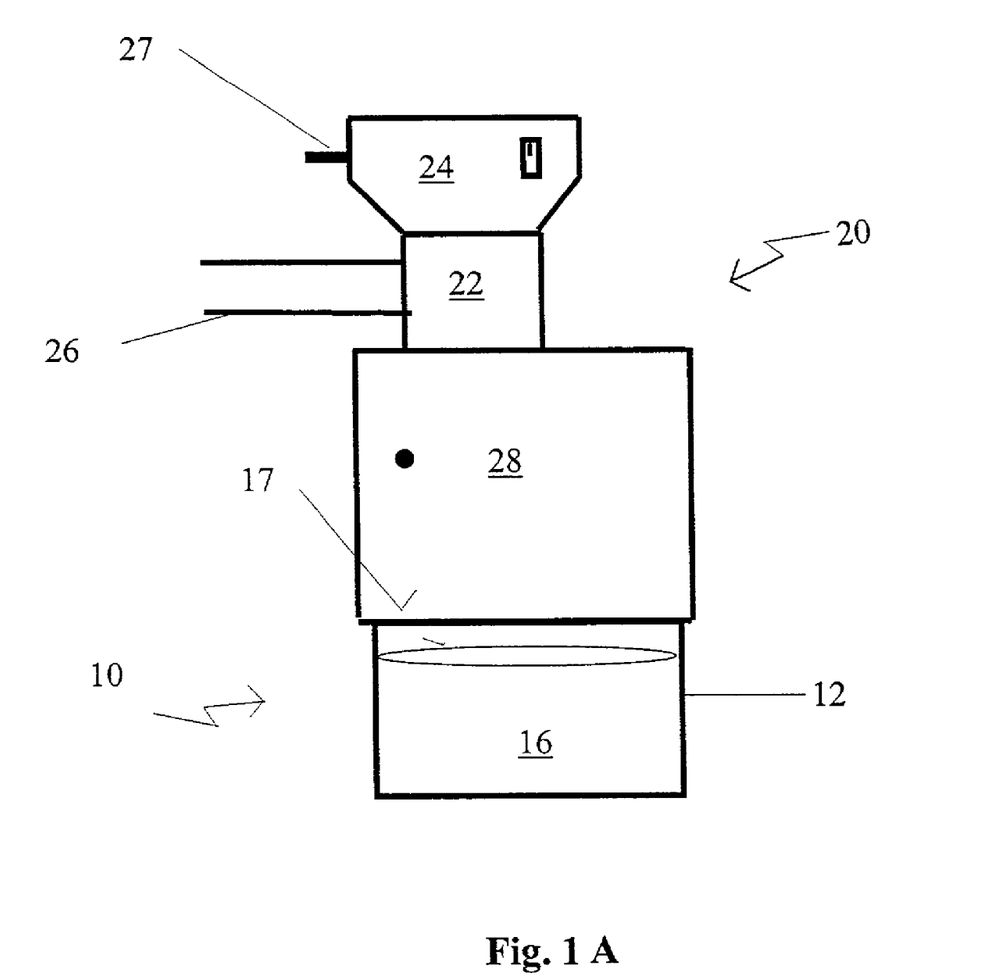

Illustrated in FIG. 1A is a side view of an endoscope disinfecting apparatus 10, including an embodiment of the ventilation system 20 of the present invention. As shown, the endoscope disinfecting apparatus 10 includes a soaking basin 12. The soaking basin 12 includes a volume of disinfecting solution 16 in which an endoscope (not shown) to be disinfected is soaked. During use of the disinfecting apparatus 10, vapors emanate from the surface 17 of the disinfecting solution 16. In an attempt to minimize the exposure of workers using the disinfecting apparatus 10 to these vapors, a fume hood 28 is provided. As such, the vapors from the disinfecting solution 16 will collect in a vapor space defined by the surface 17 of the disinfecting solution 16, the walls of the soaking basin 12, and the fume hood 28, and can be removed with the ventilation system 20 of the present invention.

In contrast, previous endoscope disinfecting apparatus tend to be tub-shaped and merely include a lid to contain vapors from the disinfecting solution rather than the ventilation system 20 of the present invention. Commonly, one or more of these previous endoscope disinfecting apparatus would be placed inside an enclosure which is in turn ventilated to remove fumes from the enclosure that are released when the lid of the endoscope disinfecting apparatus are removed. Because these enclosures must be sized such that one or more endoscope disinfecting apparatus can be accommodated as well as the arms and potentially upper torso of the worker using the apparatus, the enclosures tend to be rather large. As such, the vapors are released to an unnecessarily large area prior to their removal, meaning workers are unnecessarily exposed to those fumes. Embodiments of the present invention seek to minimize exposure to these vapors by minimizing both the surface area 17 of the disinfecting solution 16 and the volume of the vapor space, as well as providing adequate removal of the vapors with the ventilation system 20.

An embodiment of the ventilation system 20 of the present invention includes a fan (not shown), a fan housing 22, a motor (not shown), a motor housing 24, an exhaust hose 26, and a fume hood 28. As shown in FIG. 1A, the fan housing 22 is mounted directly on the fume hood 28 and is in fluid communication with the vapor space 17. As such, the fan can take suction on the vapor space in order to extract vapors therefrom, and expel the vapors through the exhaust hose 26. In this manner, the build-up of vapors during use of the disinfecting apparatus 10 is minimized, thereby minimizing the exposure of the workers to the harmful vapors when the fume hood 28 is opened to access the soaking basin 12. Embodiments are also envisioned wherein the fan housing 22 is mounted either to the soaking basin 12 or a lid 18(FIG. 1B) for the soaking basin 12, and are therefore in fluid communication with the vapor space. As well, embodiments can include a suction hose (not shown) connecting the fan housing 22 to either the lid 18 or soaking basin 12, thereby allowing the fan housing 22 to be remotely located from the endoscope disinfecting apparatus 10. Although the fan and motor are ideally disposed in separate housings, it is contemplated that both the fan and the motor could be stored within a single housing. As well, in that the motor is electric, a power cord 27 is provided.

Figure 2:
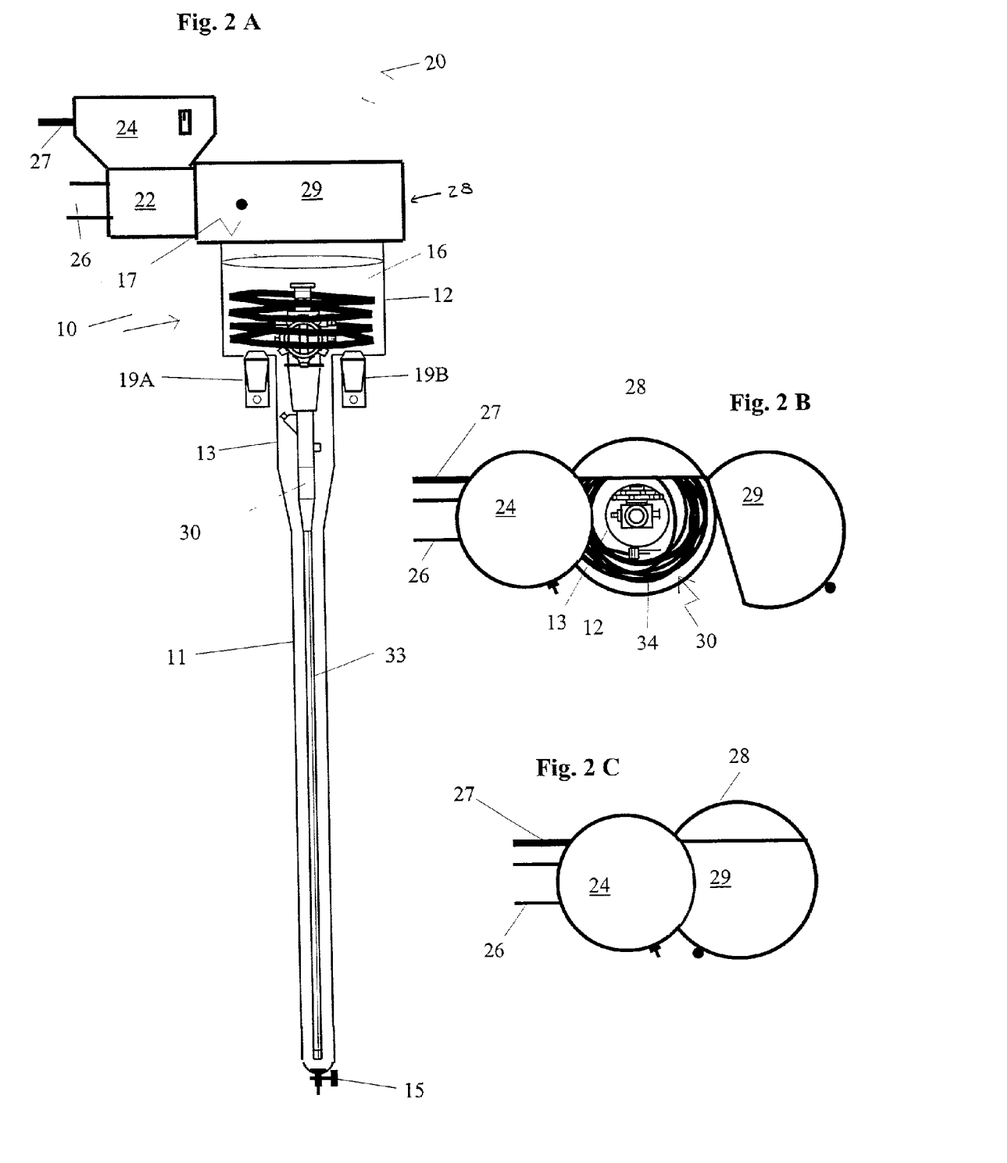
FIG. 2A is a side view of an endoscope within an endoscope disinfecting apparatus that includes the ventilation system of the present invention.
FIG. 2B is a top view of the endoscope disinfecting apparatus, as shown in FIG. 2A, with the access door open.
FIG. 2C is a top view of the endoscope disinfecting apparatus, as shown in FIG. 2A, with the access door closed.

Illustrated in FIG. 2A is a cutaway side view of one example of an endoscope disinfecting apparatus 10 including an embodiment of the ventilation system 20 of the present invention. In order to further minimize the harmful vapors that are generated by the disinfecting fluid, the ventilation system 20 can be coupled with an endoscope disinfecting apparatus 10 that is configured to minimize the surface area 17 of the disinfecting solution 16 used. The endoscope disinfecting apparatus 10 comprises many different sections to provide for disinfecting of an endoscope 30 by soaking it in a disinfecting solution 16. In the configuration shown, the endoscope disinfecting apparatus 10 is able to minimize the surface area and air exposure of the disinfecting solution 16. The endoscope disinfecting apparatus 10 enables an endoscope 30 to be disinfected by soaking the endoscope 30 in a disinfecting solution 16. The endoscope disinfecting apparatus 10 normally comprises an insertion tube section 11, a soaking basin 12, an endoscope body section 13, and a drain 15. A fume hood 28 having an access door 29 (FIGS. 2B and 2C) is included. The insertion tube section 11 is designed in the general shape, size, and length corresponding to the type of endoscope for which the endoscope disinfecting apparatus 10 is specifically designed. The insertion tube section 11 length ranges from a few centimeters to over 200 centimeters long, depending on the length of the endoscope for which the endoscope disinfecting apparatus 10 is specifically designed to disinfect. The diameter of the insertion tube section will range from ¼ inch to the three to four inch range. As shown, the insertion tube section 11 is centered in the bottom of the soaking basin 12. This is ideal if the air/water and light tube 34 can be separated from the endoscope 30. However, where the air/water and light tube 34 cannot be removed, the insertion tube section 11 can be positioned off center so that the connection between the air/water and light tube 34 and the endoscope 30 is not unduly stressed by bending.

The endoscope disinfecting apparatus 10 is further comprised of body section 13 that is connected to the insertion tube section 11. The body section 13 supports the body of the endoscope 30. The endoscope body section 13 can be configured in a range of shapes and diameters, each shape and diameter designed specifically for the intended endoscope 30. The diameter of the body of the endoscope control section 13 can range from one quarter inch to 5 inches, but will most commonly be ¾ inch to three inches (at least on human endoscopes).

The soaking basin 12 is attached to the endoscope body section 13 of the endoscope disinfecting apparatus 10. The endoscope soaking basin 12 is specifically designed to reduce the liquid surface area exposure of the disinfectant 16 to reduce the rate of evaporation of the disinfecting solution 16. The soaking basin 12 can be configured in a wide variety of shapes and sizes corresponding to the type of endoscope 30 for which it is designed. The general diameter of soaking basin 12 can range from 4 inch to 18 inches, but preferably is 4 inches to 10 inches. The soaking basin 12 has a depth of 2 inches to 10 inches, but preferably 4 inches to 8 inches.

To further reduce evaporation of the disinfecting solution 16, the endoscope disinfecting apparatus 10 further includes a fume hood 28 that includes an access door 29. This fume hood 28 may or may not connect with a water tight/air tight seal to the soaking basin 12. When a water/air tight seal exists, it may be desirable to operate the motor (not shown) only when the access door 29 is open. This could be accomplished by having an electric switch (not shown) activate the motor when the access door 29 is open and deactivate the motor when the access door 29 is closed. As well, a ventilation check valve (not shown) could be provided that prevents vapors from escaping from the fume hood 28, yet allows adequate inflow to permit operation of the motor. Manual operation of the motor is also envisioned. This fume hood 28 further prevents evaporation and spills of any toxic disinfectant solution 16 and thereby protects medical staff.

Although efforts are made to minimize the surface area of the disinfecting solution 16 used, vapors will nonetheless be generated and collect inside the fume hood 28. Therefore, the ventilation system 20 is used to remove those fumes that collect in the fume hood 28. As shown, the fan housing 22 is mounted to the fume hood 28 such that the fan (not shown) is in fluid communication with the interior of the fume hood 28. As such, the fan can be used to draw the fumes out of the fume hood 28 and expel the fumes through the exhaust hose 26. The fan can be run continuously, or intermittently, prior to opening the access door 29 of the fume hood 28. As previously noted, where a water/air tight seal exists between the fume hood 28 and the soaking basin 12, intermittent operation of the motor is probably desired. However, when the seal is not water/air tight, continuous operation of the motor during use of the endoscope disinfecting apparatus 10 is most desirable in order to minimize the release of vapors.

The endoscope disinfecting apparatus 10 further includes a draining valve 15 attached at the far end of the insertion tube section 11. The drain valve 15 enables medical staff to quickly and efficiently drain the disinfecting solution 16 from the endoscope disinfecting apparatus 10. It is also contemplated by the inventor that the drain valve 15 may be comprised of a drain plug or other type of mechanism to allow for controlled flow of the disinfecting solution 16 from the endoscope disinfecting unit 10. It is also contemplated by the inventor that the drain valve 15 may connect directly to some tube or other liquid containing mechanism to limit evaporation and further prevent medical staff from coming in direct contact with the disinfecting solution 16.

Further attached to the endoscope disinfecting apparatus 10 are mounting brackets 19A and 19B. These mounting brackets can attach to the endoscope disinfecting apparatus 10 on either side of the soaking basin 12. The mounting brackets 19A and 19B are shown for purposes of illustration only, and in fact, may be any type of mounting mechanism to support the endoscope cleaning apparatus 10.

Illustrated in FIGS. 2B and 2C are top views of the endoscope disinfecting apparatus 10. As shown, the endoscope 30 is supported by the endoscope body section 13, the insertion tube (33 in FIG. 2A) being suspended, allowing for maximum insertion tube surface contact with the disinfecting solution. The air/water and light tube 34 is coiled within the soaking basin 12. This enables the endoscope disinfecting apparatus 10 to soak and disinfect the insertion tube 33 and the air/water and light tubes 34 to further provide the cleanest possible endoscope 30 for use in a patient. The access door 29 permits the endoscope 30 to be placed in, and retrieved from, the endoscope disinfecting apparatus 10. Ideally, the access door 29 allows ample space for ease of use. Also, the access door 29 operates freely, unimpeded by the placement of the fan housing 22 on the soaking basin 12. Once the endoscope 30 has been placed inside the endoscope disinfecting apparatus 10, the access door 29 is placed in the closed position (FIG. 2C).

Figure 3:
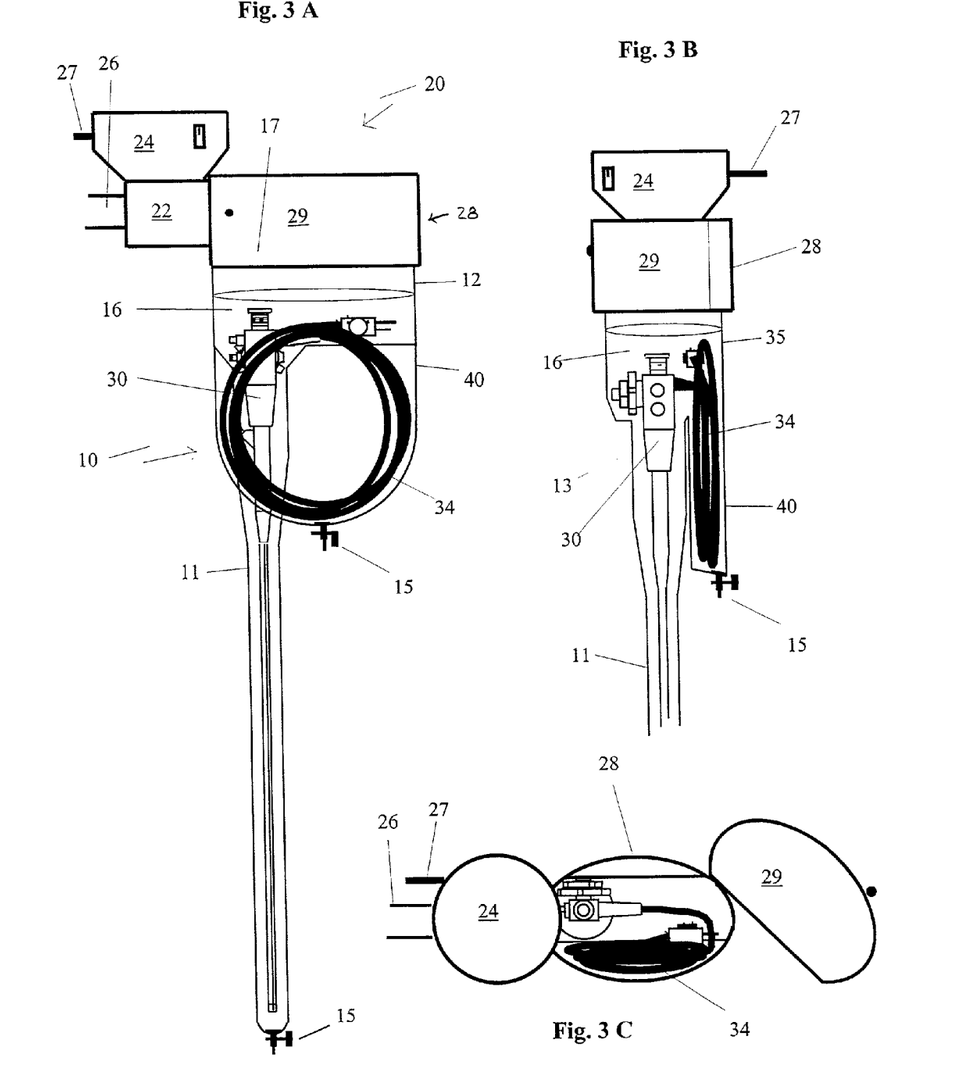
FIG. 3A is a side view of an alternative embodiment of an endoscope disinfecting apparatus with a pouch for the air/water and light cord, that includes the ventilation system of the present invention.
FIG. 3B is a side view of the endoscope cleaning apparatus, as shown in FIG. 3A.
FIG. 3C is a top view of the endoscope disinfecting apparatus, as shown in FIG. 3A, with the access door open.

Illustrated in FIG. 3A is still another alternative embodiment of an endoscope disinfecting apparatus 10 including the ventilation system 20 of the present invention. As discussed before, the endoscope disinfecting apparatus 10 is substantially similar to the endoscope disinfecting apparatus 10 previously discussed with regard to FIG. 2A. However, the distinctions between FIG. 2A will be herein discussed in detail. The first distinction of the endoscope disinfecting apparatus 10 is the addition of a pouch 40. The pouch 40 provides extra space to contain the air/water and light tube 34 that is connected to the endoscope 30 being disinfected in the endoscope disinfecting apparatus 10. By utilizing this pouch 40, the liquid surface area is further reduced as the air/water light tube 34 is coiled and turned downward. Also, less stress is put on the connection of the air/water light tube 34 with the endoscope 30.

Illustrated in FIG. 3B is another side view of the endoscope disinfecting apparatus 10 having a pouch 40. Here it is even more clearly illustrated that the air/water and light tube 34 is contained within a disinfecting solution 16, whereby the connection of the air/water light tube 34 and the endoscope 30 is not stressed. It is also depicted in FIG. 3B that the insertion tube section 11 is offset from the center of the soaking basin 12. This offset is further implemented to relieve any stress on the connection of the air/water and light tube 34 with the endoscope 30. This is further shown in the top view of FIG. 3C wherein the endoscope 30 is inserted in the endoscope disinfecting apparatus 10 and offset from the center of the soaking basin 12.

Figure 4:
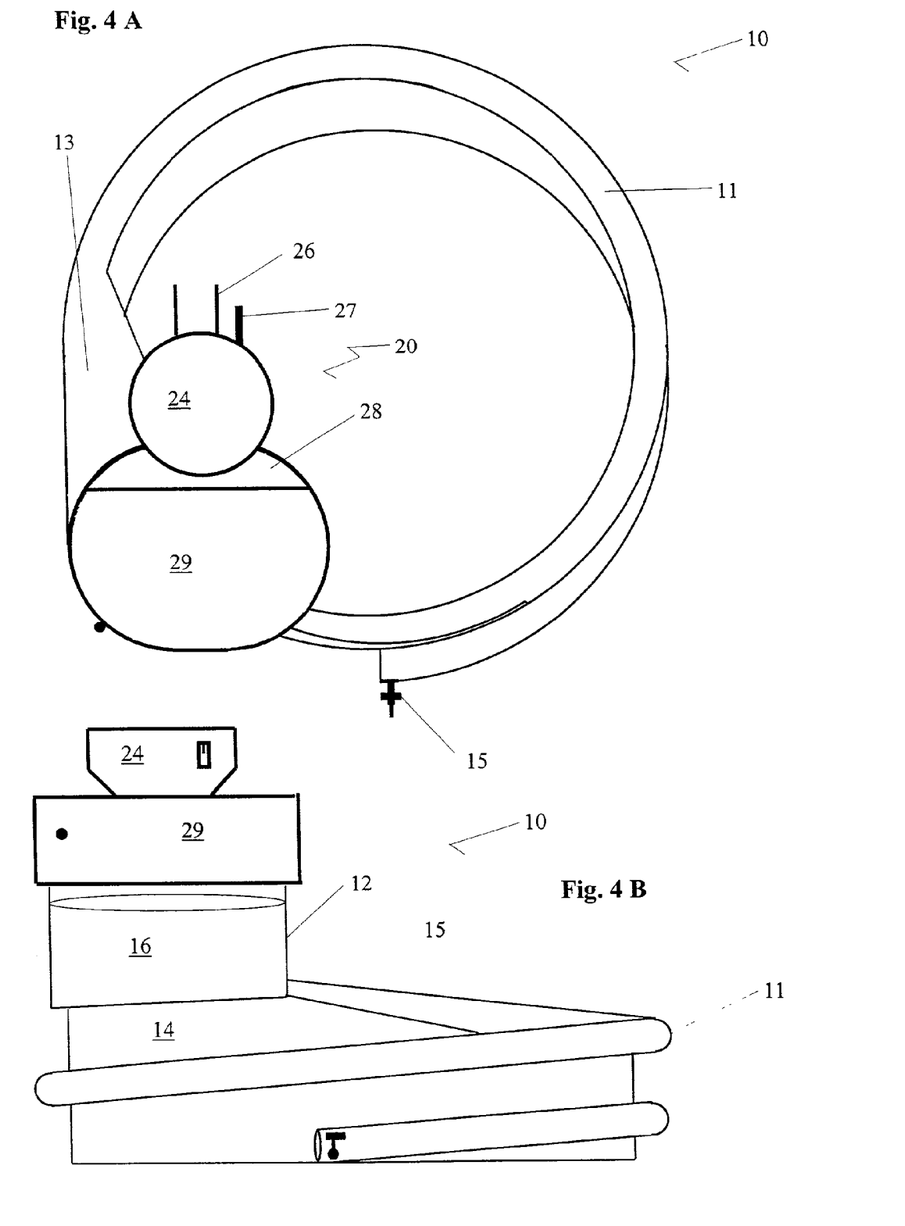
FIG. 4A is a top view of an alternative embodiment of an endoscope disinfecting apparatus having a coiled insertion tube section and including the ventilation system of the present invention.
FIG. 4B is a side view of the endoscope disinfecting apparatus as shown in FIG. 4A.

Illustrated in FIG. 4A is a top view of an alternative embodiment of the endoscope disinfecting apparatus 10 including an embodiment of the ventilation system 20 of the present invention, with the access door 29 closed. The coiled endoscope disinfecting apparatus 10 has a soaking basin 12 (FIG. 4B) connected to a body section 13. The body section 13 is further connected to the coiled insertion tube section 11. The outside diameter of the coiled endoscope disinfecting apparatus 10 ranges from a preferred range of 5 to 30 inches. Given one and three quarters coils as illustrated in FIG. 4A, an endoscope with a 220 centimeter insertion tube would require a diameter of about 17 inches across. A 160 cm insertion tube would require a diameter of about 13 inches across. A 65 cm insertion tube would require a diameter of about 10 inches. While the invention shows the insertion tube section 11 coiling one and three quarters times, it is contemplated by the inventor that the insertion tube section 11 may be coiled through one half to five turns. Attached at the lowest point of the coiled endoscope disinfecting apparatus 10 is the drain valve 15.

Illustrated in FIG. 4B is a side view of the coiled endoscope disinfecting apparatus 10. Shown is the fume hood 28 that is connectable to the soaking basin 12. As stated before, the fume hood 28 enables a medical staff member to prevent the escape of any disinfecting solution 16 or vapors from the disinfecting solution. From an ease of construction standpoint, the insertion tube section 11 is shown coiled about a support cylinder 14. Note, however, multiple configurations are envisioned that allow the endoscope disinfecting apparatus 10 to rest firmly on a support surface. For example, rather than utilizing a support cylinder 14, the coils of the insertion tube section 11 could be separated by support struts (not shown) or simply allowed to rest one on top of another. It is contemplated by the inventor that the enlargement of the soaking basin 12, the body section 13 and the insertion tube section 11 would allow two or more endoscopes to be disinfected at the same time.

Figure 5:
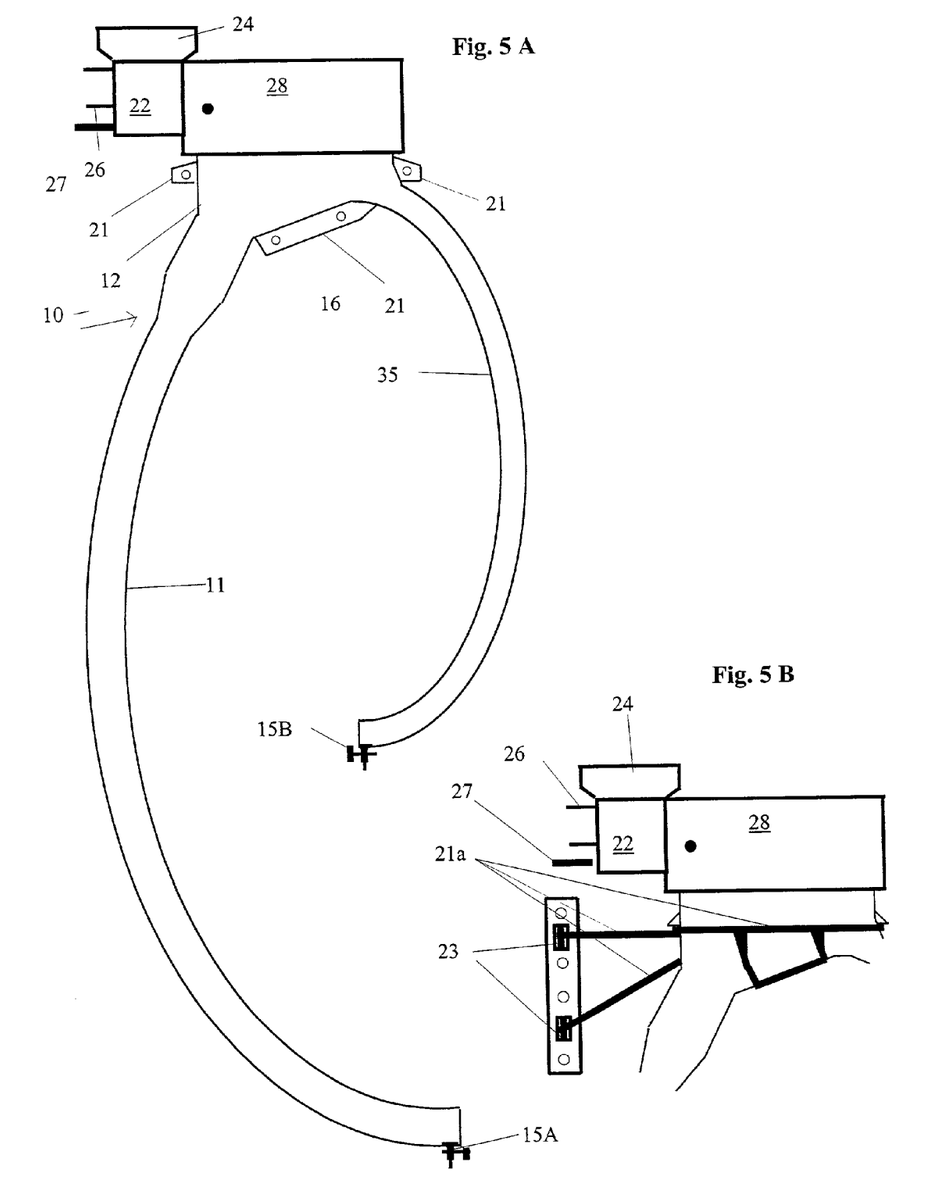
FIG. 5A is a side view of a hanging alternative embodiment of an endoscope disinfecting apparatus including the ventilation system of the present invention.
FIG. 5B is a partial side view of the endoscope disinfecting apparatus shown in FIG. 5A, further including an alternative mounting bracket.

Illustrated in FIG. 5A is a hanging version of the endoscope disinfecting apparatus 10. One difference from the other embodiments of the endoscope disinfecting apparatus 10 is that the insertion tube section 11 and universal tube section 35 are curved to match the curvature of the endoscope (not shown) and air/water and light tube. The endoscope disinfecting apparatus 10 is curved so that longer endoscopes could be inserted more easily. The curve allows a shorter distance to the ground, thereby allowing the endoscope soaking apparatus 10 to be mounted to a support surface at a convenient height. For example, the integrally formed mounting brackets 21 could be used such that the top of the soaking basin 12 could be brought down to somewhere between elbow and shoulder level. Also, the curve allows a slanted angle to put the scope in, easier especially for a shorter person. Also illustrated in FIG. 5 are drainage valves 15A and 15B that are positioned at the lowest point of the insertion tube section 11 and the universal tube section 35. This arrangement enables a medical staff member to drain the disinfecting solution 16 from the endoscope disinfecting apparatus 10 without moving or tipping the endoscope disinfecting apparatus 10. As discussed previously with regard to FIG. 1A, the drainage valves 15A and 15B could comprise any type of valve or plug for controlling the flow of disinfecting solution 16. It is also contemplated by the inventor that drainage valves 15A and 15B are connectable to a tube to further limit the medical staff from coming into contact with the disinfecting solution 16.

Illustrated in FIG. 5B is a partial side view of the curved endoscope disinfecting apparatus 10 and an alternative mounting bracket 21a. It is contemplated by the inventor that the mounting bracket 21a for the endoscope disinfecting apparatus 10 could be a hinged unit that would allow the endoscope disinfecting apparatus 10 to be rotated closer to a wall or solid surface on hinges 23.

Figure 6:
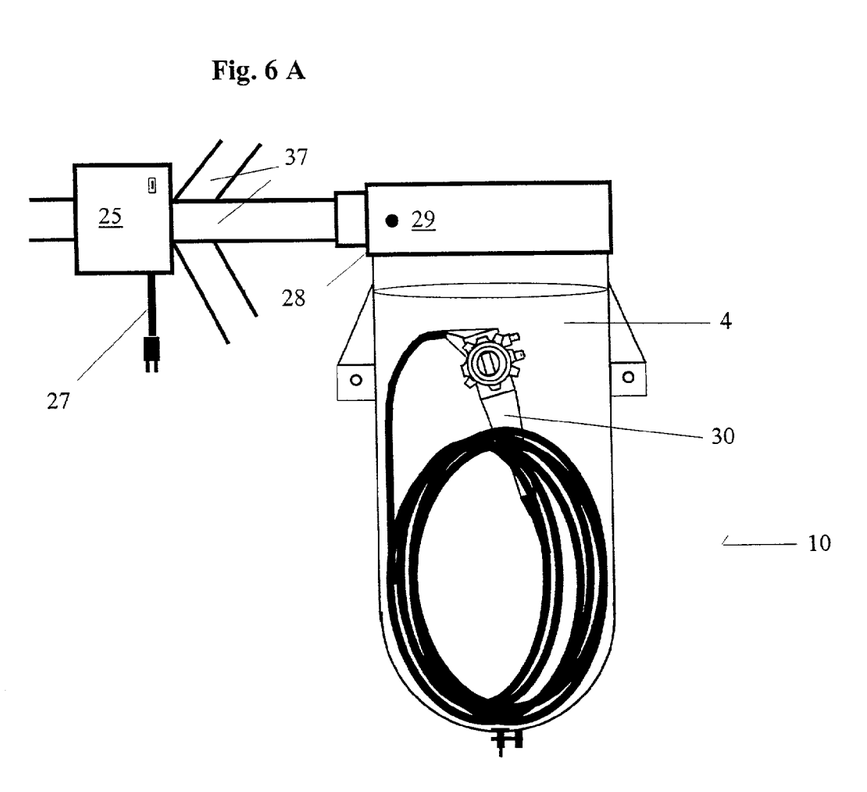
FIG. 6A is a side view of an embodiment of the ventilation system of the present invention, where the ventilation system is remote from the endoscope disinfecting apparatus.
FIG. 6B is a top view of the endoscope disinfecting apparatus, as shown in FIG. 6A, with the access door open.

Illustrated in FIG. 6A is an embodiment of the present invention wherein a single fan (not shown) can be used to ventilate the vapors from multiple fume hoods 28 (FIG. 6B). In order to accomplish this feat, multiple suction hoses 37 are provided, each suction hose 37 being connected at one end to a fume hood 28 and at the other end to the fan/motor housing 25. Note that in the embodiment shown, a single fan/motor housing 25 is provided, rather than separate housings for both the fan and the motor. Also note that the fan/motor housing 25 is remotely located from the individual fume hoods 28. This facilitates the configuration wherein multiple fume hoods 28 are ventilated by a single fan. It is contemplated by the invention that the suction hoses 37 could be attached at one end to the endoscope disinfecting apparatus 10 rather than the fume hood 28.

FIG. 6B is a top view of the endoscope disinfecting apparatus 10, as shown in FIG. 6A, with the access door 29 to the fume hood 28 in the open position.

Figure 7:
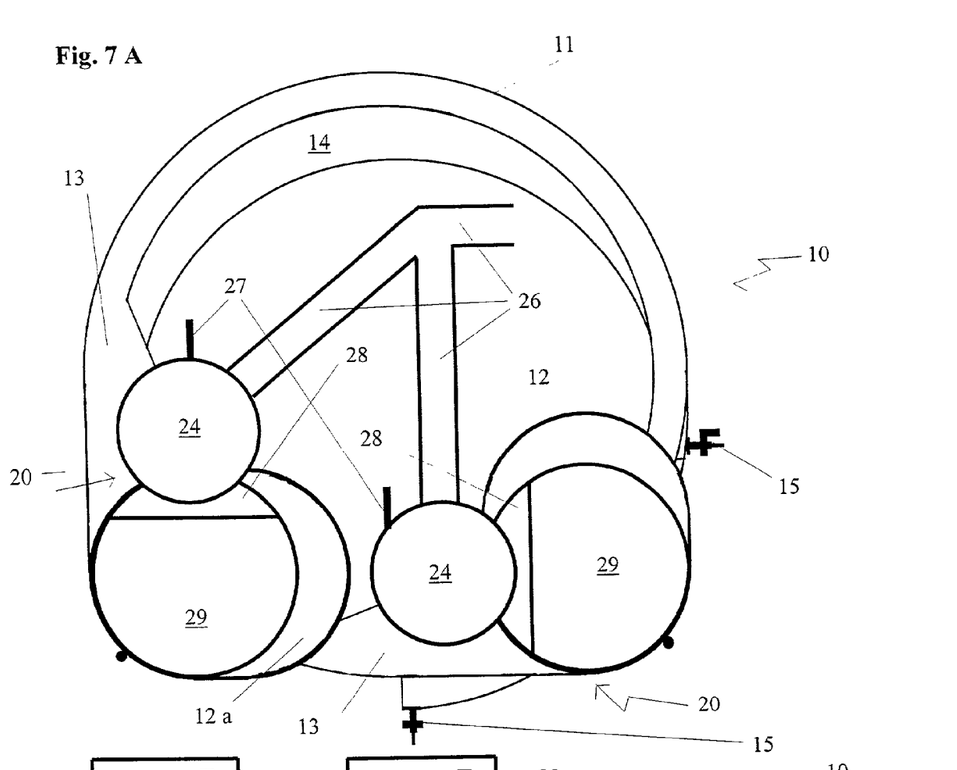
FIG. 7A is a top view of an alternative embodiment of a dual endoscope disinfecting apparatus wherein each has a coiled insertion tube section and includes the ventilation system of the present invention.
FIG. 7B is a side view of the endoscope disinfecting apparatus as shown in FIG. 7A.

Illustrated in FIG. 7A is an embodiment of the present invention wherein two endoscope disinfecting apparatus 10, similar to those shown in FIG. 4A, have been formed about a single support cylinder 14 in order to conserve space. As shown, each endoscope disinfecting apparatus 10 includes an individual ventilation system 20 that exhausts through a common exhaust hose 26.

FIG. 7B is a side view of the dual endoscope disinfecting apparatus 10, as shown in FIG. 7A. Note that the soaking basins 12 are configured such that an expanded section 12a are configured such that an expanded section 12a protrudes from the side of the soaking basin 12 under the point at which the surface 17 of the disinfecting solution 16 is located. This allows the volume of the soaking basin to be maximized while at the same time minimizing the surface area of the disinfecting solution.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of the present invention and protected by the following claims.

What is claimed is:

1. An exhaust system for removing fumes from an endoscope disinfecting apparatus configured for disinfecting an endoscope with a disinfecting solution, said exhaust system comprising:
    a soaking basin;
    a basin lid;
    a fan housing;
    a fan disposed within said fan housing;
    an exhaust hose connected to said fan housing; and
    wherein said exhaust system is connected to said endoscope disinfecting apparatus and further includes a suction hose having a first end and a second end, said first end being connected to said lid and said second end being connected to said fan housing such that said fan is communicatively coupled to a vapor space.

2. The system of claim 1, wherein said lid being configured to contain fumes from the disinfecting solution within said vapor space defined by said lid, said soaking basin, and a surface of the disinfecting solution.

3. The system of claim 2, wherein said fan housing is connected to said soaking basin such that said fan is communicatively coupled to said vapor space.

4. The system of claim 3, wherein said fan removes said fumes from said vapor space and exhausts said fumes through said exhaust hose.

5. The system of claim 2, wherein said fan housing is connected to said lid such that said fan is communicatively coupled to said vapor space.

6. The system of claim 2, wherein said exhaust system further includes a plurality of suction hoses and a plurality of endoscope disinfecting apparatus each of said plurality of suction houses communicatively coupling one of said plurality of endoscope disinfecting apparati with said fan housing.

7. The system of claim 1, wherein said exhaust system further includes a second suction hose having a first end and a second end, said first end being connected to said soaking basin and said second end being connected to said fan housing such that said fan is communicatively coupled to said vapor space.

8. The system of claim 1, wherein said exhaust system further includes a motor for driving said fan, said motor being disposed within a motor housing, said motor housing being connected to said fan housing.

9. The system of claim 1, wherein said fan is an electric fan.

10. An exhaust system for removing fumes from an endoscope disinfecting apparatus configured for disinfecting an endoscope with a disinfecting solution, said exhaust system comprising:
   a fume hood to provide a vapor containment space over said endoscope disinfecting apparatus;
   a fan housing;
   a fan disposed within said fan housing;
   an exhaust hose connected to said fan housing;
   a disinfecting basin that disinfects an air/water and light tube of the endoscope;
   an endoscope body section connected to said disinfecting basin that disinfects a body and eye piece of the endoscope;
   wherein said disinfecting basin is a pouch connected to a side of said endoscope body section and wherein said fan housing is communicatively coupled to said fume hood such that fumes can be removed from said vapor containment space by said exhaust system.

11. The system of claim 10, wherein said fume hood further includes an access door that permits access to said endoscope disinfecting apparatus for insertion and removal of the endoscope.

12. The system of claim 10, wherein said fan housing is mounted on said fume hood.

13. The system of claim 10, further including a suction hose having a first end and a second end, said first end being connected to said fume hood and said second end being connected to said fan housing.

14. The system of claim 10, further including a plurality of suction hoses, each of said suction hoses having a first end and a second end, each of said first ends being adapted and configured for attachment to one of said plurality of fume hoods, and each of said second ends being connected to said fan housing.

15. The system of claim 10, wherein said endoscope disinfecting apparatus further comprises:
   an insertion tube section connected to said endoscope body section that disinfects an insertion tube of the endoscope.

16. The system of claim 15, wherein said insertion tube section is coiled.

17. The system of claim 16, wherein said endoscope disinfecting apparatus further comprises a support cylinder and said insertion tube section is coiled around said support cylinder.

18. The system of claim 16, wherein said insertion tube section is coiled between ½ and 5 turns.

* * * * *